United States Patent [19]

Sogawa et al.

[11] Patent Number: 5,308,323
[45] Date of Patent: May 3, 1994

[54] MULTIPLE COMPARTMENT BALLOON CATHETER

[75] Inventors: Ichiro Sogawa; Shin-ichiro Niwa; Koro Yotsuya; Takafumi Uemiya; Shin-ichi Kanazawa, all of Osaka, Japan

[73] Assignee: Sumitomo Electric Industries. Ltd., Osaka, Japan

[21] Appl. No.: 24,864

[22] PCT Filed: Jun. 6, 1989

[86] PCT No.: PCT/JP89/00575

§ 371 Date: Feb. 6, 1990

§ 102(e) Date: Feb. 6, 1990

[87] PCT Pub. No.: WO89/11889

PCT Pub. Date: Dec. 14, 1989

Related U.S. Application Data

[63] Continuation of Ser. No. 465,087, Feb. 6, 1990, abandoned.

[30] Foreign Application Priority Data

Jun. 6, 1988 [JP] Japan .................... 63-74906[U]

[51] Int. Cl.$^5$ .................... A61M 37/00; A61M 29/00
[52] U.S. Cl. ............................ 604/95; 604/96; 604/101; 606/192; 606/194
[58] Field of Search ............... 604/95, 96, 104; 606/7, 606/191-200; 128/207.14, 207.15

[56] References Cited

U.S. PATENT DOCUMENTS

| | | | |
|---|---|---|---|
| 4,141,364 | 12/1979 | Schultze | 128/207.15 |
| 4,183,102 | 1/1980 | Guiset | 604/101 |
| 4,327,720 | 5/1982 | Bronson et al. | 128/207.15 |
| 4,406,656 | 9/1983 | Hattler et al. | 604/96 |
| 4,581,017 | 4/1986 | Sahota | 604/101 |
| 4,878,495 | 11/1989 | Grayzel | 604/101 |
| 4,958,364 | 9/1990 | Jang | 604/103 |
| 5,102,416 | 4/1992 | Rock | 604/194 |

FOREIGN PATENT DOCUMENTS

| | | |
|---|---|---|
| 0231725 | 8/1987 | European Pat. Off. |
| 0261831 | 3/1988 | European Pat. Off. |
| 57-23506 | 5/1982 | Japan |
| 846779 | 8/1960 | United Kingdom ...... 604/194 |

*Primary Examiner*—C. Fred Rosenbaum
*Assistant Examiner*—Mark Bockelman
*Attorney, Agent, or Firm*—Cushman, Darby & Cushman

[57] ABSTRACT

A catheter provided on the tip with a balloon of the type which can be inflated by being filled with a fluid, and particularly a catheter provided with a balloon around the inside circumference of which are formed multiple compartments. The direction of said catheter can be controlled at bifurcations in the blood vessel by supplying fluid through a fluid supply channel to at least one compartment so as to inflate the compartment corresponding to said channel.

2 Claims, 1 Drawing Sheet

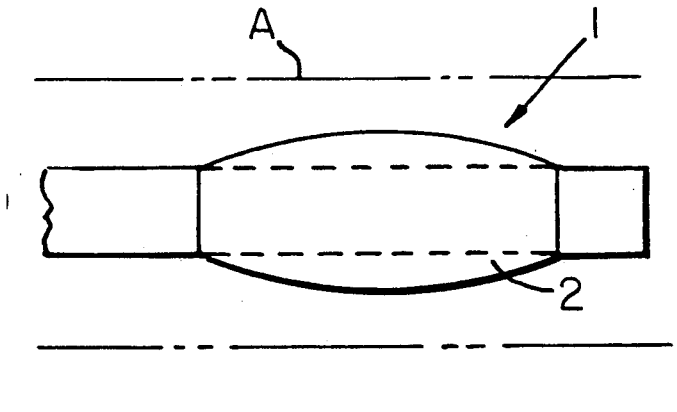
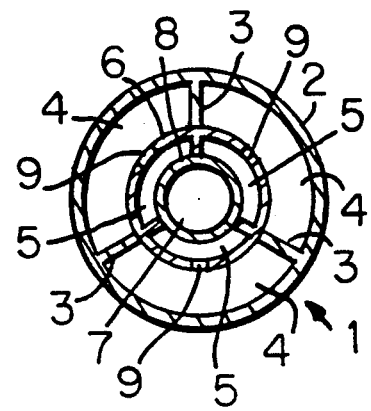
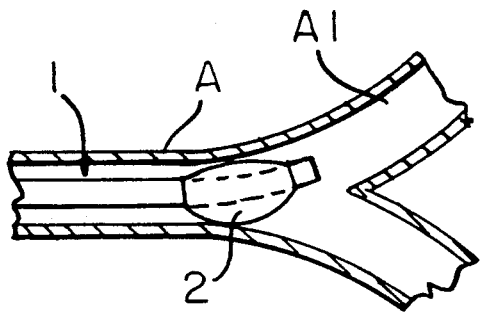
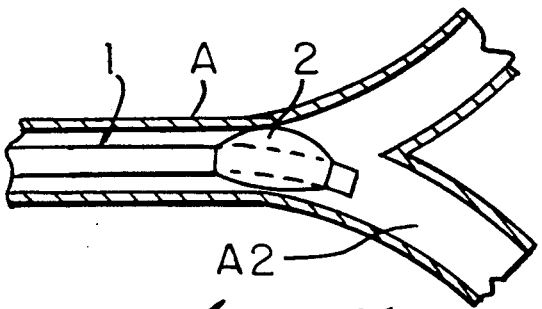
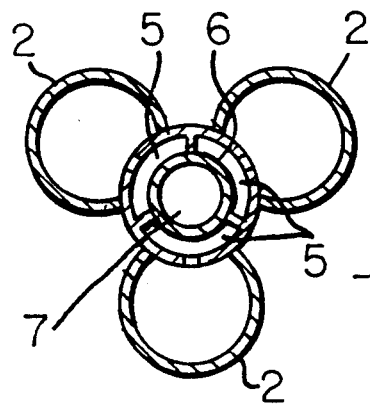

MULTIPLE COMPARTMENT BALLOON CATHETER

This is a continuation of application Ser. No. 07/465,087, filed on Feb. 6, 1990, which is abandoned.

DESCRIPTION

1. Technical Field

The present invention relates to a catheter, and particularly to a catheter which is inserted into the blood vessels, urethra, and similar vessels of the body.

2. Background Art

Various methods have been developed for the treatment of arterial and vascular constriction or occlusion due to arteriosclerosis, and for the removal of thrombi.

The most widely used method is bypass surgery in which the lesioned member of the blood vessel is surgically removed and replaced with a section of blood vessel from the patient or with an artificial blood vessel, thus physically eliminating the problem. However, because this procedure necessitates cutting the body open, the load on the body is great and treatment incurs great cost.

Drug therapy is also employed, but this is only effective for dissolving thrombi, and is not very successful at removing arteriosclerotic foci or occlusions.

New alternative methods selectively employed include the insertion of a catheter with a balloon into the blood vessel and inflating the balloon at the site of the lesion to mechanically enlarge the blood vessel at the constricted site, and the insertion of a catheter with a balloon in which is carried an optical fiber for laser conduction. In this latter method, the balloon is inflated to occlude the blood vessel and stop the blood f low while the laser is used to evaporate the lesion.

Diagnostic techniques employed with the inside wall of the blood vessels includes the insertion of a catheter containing an imaging fiber into the blood vessel to inspect lesions using said imaging fiber.

In the use of such a catheter for therapy or diagnosis as previously described, it must be possible to steer the catheter in the desired direction at blood vessel bifurcations in order for the catheter to reach the site of the target lesion.

This is presently accomplished by using a catheter the leading end of which is bent to a specific angle. The catheter is steered by rotating the hand-held end of the catheter to align the leading end with the branch vessel down which the catheter is to be conducted. However, large individual differences in the shape and condition of said bifurcations make it difficult to use catheters of the above construction with all patients, and it is also difficult to conduct the catheter down the desired branch at complex, multi-branched junctions.

It has therefore been proposed to use a jointed ring construction on the catheter end and to steer the catheter in the desired direction by operating a wire passing through the catheter. However, because the construction of such a catheter is complex, it is difficult to achieve a fine diameter catheter.

With respect the aforementioned problems, a catheter according to the present invention provides a construction which is simple and which can be easily conducted in the desired direction through blood vessels and other vessels of the body.

DISCLOSURE INVENTION

A catheter according to a first embodiment of the present invention is comprised of multiple compartments along the circumference of the inside of the balloon, and individual fluid supply channels provided for each compartment.

A catheter according to a second embodiment of the present invention is comprised of multiple balloons along the circumference of the catheter, and individual fluid supply channels provided for each balloon.

Using a catheter according to said first embodiment, the catheter tip can be aligned in the desired direction when the catheter is inserted into a blood vessel or similar vessel by supplying a fluid to a specific compartment through the fluid supply channels and thus inflating that compartment.

Furthermore, using a catheter according to said first embodiment, the catheter tip can be aligned in the desired direction by likewise supplying a fluid to a specific balloon to inflate said balloon.

BRIEF DESCRIPTION OF DRAWINGS

FIG. 1 is a front view of a first embodiment of a catheter according to the present invention, FIG. 2 is a cross section of said first catheter, FIG. 3 and FIG. 4 are cross sections showing said catheter in use, and FIG. 5 is a front view of an alternative catheter.

BEST MODE FOR CARRYING OUT THE INVENTION

FIG. 1 is a front view showing the front tip of a catheter 1 according to the present invention. Said tip is comprised of a balloon 2 which is used to occlude vessel A, which may be a blood vessel or similar vessel. Inside said balloon 2 is formed multiple compartments 4 which are divided by radial walls 3 as shown in FIG. 2. A channel 5 for fluid supply is individually provided to each of compartments 4 so that a gas or fluid may be supplied separately and individually to each of compartments 4 via said channel 5 through openings 9 in the wall of tube 6 in order to inflate that compartment 4. Said fluid supply channels 5 are formed by compartmentalizing the inside of a single tube 6 as shown in the figure according to the number of compartments 4 provided. Inside of tube 6 may be used as a channel 7 for the supply of drugs, the channel 7 being bounded by second tube 8.

If the catheter 1 is construed as just described, when the catheter 1 is inserted into vessel A and is advanced to a bifurcation or other juncture in vessel A, the tip of catheter 1 can be aligned in the desired direction and conducted down the desired branch vessel by selectively inflating compartments 4.

Specifically, if, as shown in FIG. 3, inflation fluid is supplied to the compartment 4 which is opposite the bottom wall of vessel A on the inside of the vessel so that said compartment 4 is inflated, when the bottom side of balloon 2 contacts the inside wall of vessel A, the tip of catheter 1 will be lifted and aligned with the branch which is diagonally above the bifurcation point. Therefore, said catheter 1 can be inserted into branch vessel A1 by inserting the catheter 1 farther. Furthermore, as shown in FIG. 4, if the compartment 4 opposite the top inside wall of vessel A is inflated, when the top side of the balloon 2 contacts the inside wall of vessel A, the tip of the catheter 1 will be forced down and aligned with the branch which is diagonally below the bifurcation point. Therefore, said catheter 1 can be inserted into branch vessel A2 by inserting the catheter 1 farther. Thus, the angle of orientation of the tip of catheter 1 can be freely adjusted by controlling the amount by which compartment 4 is inflated in each of the above situations. Furthermore, the orientation and direction of the catheter 1 can also be freely adjusted by appropriately inflating multiple compartments 4 at the same time.

FIG. 5 is a cross section of an alternative embodiment of catheter 1. It differs from the embodiment previously described in that multiple balloons 2 are provided diametrically along catheter 1, and fluid supply channels 5 are provided individually and separately to each of said balloons 2.

As with the previous embodiment of catheter 1, the catheter 1 tip can be aligned in the desired direction and conducted down the desired branch vessel by selectively inflating balloons 2 when the catheter 1 tip reaches the bifurcation of vessel A.

A catheter 1 according to the present invention is not limited to the above embodiments, however, and may be constructed, for example, with multiple individual tubes for each of the required fluid supply channels 5, and the construction may be changed by increasing the number of compartments 4 and balloons 2 without changing the intent and meaning of the invention.

INDUSTRIAL APPLICABILITY

A catheter 1 according to the present invention is also suited to endoscope catheters in which an imaging fiber is imbedded in the catheter, laser illumination catheters in which a laser conducting fiber is imbedded in the catheter, and other types of catheters.

A catheter according to the present invention as previously described offers the benefit of being easily conducted to the target site because the catheter can be aligned in any desired direction at any desired angle by selectively inflating any of multiple compartments inside a balloon or by selectively inflating any of multiple balloons. In addition, the additional benefit of being able to achieve fine diameter catheters can be provided because the construction is simple.

We claim:

1. A catheter comprising:
    a tube sized so as to be capable of being inserted into a vessel of the human body, said tube having partitions for dividing said tube into a plurality of channels for carrying a first fluid, said tube having a tip disposed at an end thereof;
    a balloon disposed about said tip of said tube, said balloon including radial walls defining multiple compartments, said compartments being disposed between said walls inside of said balloon, each compartment corresponding to a respective channel of said tube, said balloon compartments further including separation walls defined by said tube for separating said compartments from corresponding channels, each said separation wall having an opening so that each compartment can be selectively inflated by directing fluid into a corresponding channel and through said opening enabling the position of said catheter to be controlled by contact with a wall of said vessel.

2. A catheter as claimed in claim 1 wherein inside of said tube is disposed a second tube used as a channel for carrying a supply of drugs to a predetermined location within the vessel.

* * * * *